(12) United States Patent
Aono et al.

(10) Patent No.: US 6,576,668 B1
(45) Date of Patent: Jun. 10, 2003

(54) REMEDIES FOR ARTHROSIS DEFORMANS

(75) Inventors: Hiroyuki Aono, Osaka (JP); Miwa Takai, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/018,772

(22) PCT Filed: Jun. 21, 2000

(86) PCT No.: PCT/JP00/04051

§ 371 (c)(1), (2), (4) Date: Dec. 17, 2001

(87) PCT Pub. No.: WO00/78305

PCT Pub. Date: Dec. 28, 2000

(30) Foreign Application Priority Data

Jun. 21, 1999 (JP) .......................................... 11-173875

(51) Int. Cl.⁷ ............................................. A61K 31/195
(52) U.S. Cl. ....................................................... 514/562
(58) Field of Search ........................................ 514/562

(56) References Cited

U.S. PATENT DOCUMENTS

| | | |
|---|---|---|
| 5,266,595 A | 11/1993 | Baba et al. |
| 6,025,393 A | 2/2000 | Kitano |

FOREIGN PATENT DOCUMENTS

| | | |
|---|---|---|
| JP | 55-51020 A | 4/1980 |
| JP | 56-5388 B2 | 2/1981 |
| JP | 60-11888 B2 | 3/1985 |
| JP | 62-13922 B2 | 3/1987 |
| JP | 63-13964 B2 | 3/1988 |
| JP | 2-96521 A | 4/1990 |
| JP | 4-154721 A | 5/1992 |
| JP | 4-154722 A | 5/1992 |
| JP | 4-342524 A | 11/1992 |
| JP | 5-186341 A | 7/1993 |
| JP | 7-223944 A | 8/1995 |
| JP | 10-158160 A | 6/1998 |
| JP | 10-324625 A | 12/1998 |
| JP | 11-71272 A | 3/1999 |

OTHER PUBLICATIONS

Ishiguro et al, "Matrix Metalloproteinases, Tissue Inhibitors of Metalloproteinases, . . . ", *The Journal of Rheumatology*, Jan. 1999, vol. 26, No. 1, pp. 34–40.

Ishiguro et al, "Determination of Stromelysin–1, 72 and 92 kDA Type IV Collagenase, Tissue Inhibitor . . . ", *Journal of Rheumatology*, 1996, vol. 23, No. 9, pp. 1599–1604.

Rosen et al, "Differential Effects of Aging on Human Chondrocyte Responses to Transforming Growth Factor β", *Arthritis & Rheumatism*, Jul. 1997, vol. 40, No. 7, pp. 1275–1281.

Mehraban et al, "Osteoarthritis and Cartilage—Increase secretion and activity of matrix metalloproteinase–3 in synovial tissues", 1998, vol. 6, pp. 286–294.

Blanco et al, "Osteoarthritis Chondrocytes Die by Apoptosis", *Arthritis & Rheumatism*, Feb. 1998, vol. 41, No. 2, pp. 284–289.

Primary Examiner—Theodore J. Criares
Assistant Examiner—Jennifer Kim
(74) Attorney, Agent, or Firm—Frishauf, Holtz, Goodman & Chick, P.C.

(57) ABSTRACT

An object of the present invention is to find further new pharmacological actions of useful mercaptoacylcysteine derivatives. The present invention relates to therapeutic agents for osteoarthritis comprising compounds represented by the following general formula [I] or salts thereof as active ingredients. In the formula, "A" is lower alkylene. The lower alkylene is exemplified by straight-chain or branched alkylene having one to six carbon atoms such as methylene, ethylene, (dimethyl)methylene or (diethyl)methylene.

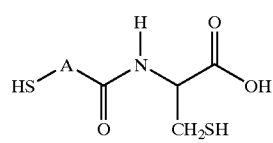

[I]

3 Claims, No Drawings

REMEDIES FOR ARTHROSIS DEFORMANS

This application is a U.S. National Phase Application under 35 USC 371 of International Application PCT/JP00/04051 (not published in English) filed Jun. 21, 2000.

TECHNICAL FIELD

The present invention relates to therapeutic agents for osteoarthritis comprising mercaptoacylcysteine derivatives as active ingredients.

BACKGROUND ART

Osteoarthritis (OA) is a disease characterized by destruction of a joint accompanied by degeneration of cartilage in a joint due to aging and progressive degradation due to mechanical stress, and by a proliferative change of bone cartilage.

A diseased part of osteoarthritis is limited to the joint, mainly a load joint. Unlike systemic autoimmune diseases such as rheumatic diseases, a synovial fluid of osteoarthritis is noninflammatory. Abnormal remarks are scarcely observed in its peripheral blood, generally an erythrocyte sedimentation rate value and a CRP value are normal, and a rheumatic factor is negative.

With regard to pathogeneses of osteoarthritis, various possibilities have been suggested by previous studies.

One of them is a lowering of an essential function of cartilage due to a decrease in chondrocytes, partial softening of chondromucoid, a decrease in water content in a cartilage substrate or a change in collagen reticular structure with aging, or a lowering of collagen synthesis due to a lowering of sensitivity of chondrocytes to transforming growth factor β (TGF-β), which plays an important role in chondrocytes (Arthritis Rheum., 40, 1275–1281 (1997)).

On the other hand, production of matrix metalloproteinase (MMP) from chondrocytes advances owing to imbalance of a joint or mechanical stress on chondrocytes due to various causes or by cytokines such as interleukin-1β (IL-1β), and MMP degrades a matrix to cause cartilage denaturation. Actually, it is considered that MMP production from cartilage tissues of patients with osteoarthritis or experimental chondrocytes is a main cause of osteoarthritis. In particular, it is known that MMP-1 and MMP-8 not only degrade collagen but also activate a variety of gelatinase, which degrades collagen completely. Further, it was reported that MMP-3 has degradative activity on proteoglycan, collagen and link protein, which play important roles in cartilage tissues, and MMP-3 exhibits the activity strongly in patients with osteoarthritis and model animals as well (Osteoarthr. Car., 6, 286–294 (1998)).

Further, as third pathogenesis, it was recently reported that chondrocytes death due to apoptosis of chondrocytes by stress, cytokines, nitric oxide (NO) or the like participates in osteoarthritis (Arthritis Rheuma., 41, 284–289 (1998)).

It was reported that mercaptoacylcysteine derivatives, which are active ingredients of the present invention, have various actions as medicines. Examples of the action are a sputum dissolving action (Japanese Examined Patent Publication No. 5388/1981), an antirheumatic action (Japanese Examined Patent Publication No. 11888/1985), a cataract therapeutic action (Japanese Examined Patent Publication No. 13922/1987), a liver disorder inhibitory action (Japanese Examined Patent Publication No. 13964/1988), an uveitis therapeutic action (Japanese Laid-open Patent Publication No. 96521/1990), a diabetes therapeutic action (Japanese Laid-open Patent Publication No. 154721/1992), an osteoporosis therapeutic action (Japanese Laid-open Patent Publication No. 154722/1992), a kidney disease therapeutic action (Japanese Laid-open Patent Publication No. 342524/1992), a cystinuria therapeutic action (Japanese Laid-open Patent Publication No. 186341/1993), an inflammatory enteropathy therapeutic action (Japanese Laid-open Patent Publication No. 223944/1995), a delayed allergy inhibitory action (Japanese Laid-open Patent Publication No. 158160/1998), an endothelium growth factor inhibitory action (Japanese Laid-open Patent Publication No. 324625/1998), a corneal neovasculature proliferation inhibitory action (Japanese Laid-open Patent Publication No. 712272/1999) and the like. Among them, bucillamine has already been marketed as pharmaceuticals, and its pharmaceutical utility has already been proved. However, there has been no report concerning its action on osteoarthritis.

It is a very interesting subject to find further new pharmacological actions of these mercaptoacylcysteine derivatives being useful as pharmaceuticals.

DISCLOSURE OF THE INVENTION

In order to find new pharmacological actions of mercaptoacylcysteine derivatives, the present inventors studied their actions on MMP-3 production of chondrocytes and degradation of proteoglycan as actions on cartilage of a joint. As a result, it was found that these mercaptoacylcysteine derivatives have MMP-3 production inhibitory actions and proteoglycan degradation inhibitory actions and are useful as therapeutic agents for diseases in which MMP participates, particularly osteoarthritis. It is known that arthrogryposis occurs and a mobility of a joint decreases in patients with osteoarthritis. Then, effects of the mercaptoacylcysteine derivatives on arthrogryposis were evaluated by using rabbit-immobilized models. As a result, a high improvement effect was found also in these rabbit-immobilized models.

The present invention provides therapeutic agents for osteoarthritis comprising compounds represented by the following general formula [I] or salts thereof (hereinafter referred to as "the present compound") as active ingredients,

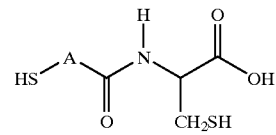

[I]

wherein "A" is lower alkylene.

The group defined above is described in more detail. The lower alkylene is straight-chain or branched alkylene having one to six carbon atoms such as methylene, ethylene, (dimethyl)methylene or (diethyl)methylene.

Salts in the present invention refer to any pharmaceutically acceptable salts. Examples thereof are salts with an alkali metal or an alkaline-earth metal such as sodium, potassium or calcium; ammonium salts; salts with an organic amine such as diethylamine or triethanolamine; and the like. The present compounds can be in the form of hydrates. There are diastereo isomers and optical isomers in the present compounds, and all of them are included in the present invention. When an optically active starting material for synthesis is used, a single diastereo isomer and a single optical isomer are obtained. When a racemate is used as a starting material, respective isomers can be separated by conventional methods, for example, a method of using an optical resolving agent or the like.

A particularly preferred example of the present compound is bucillamine represented by the following formula [II].

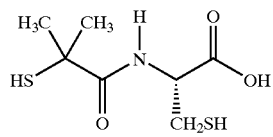

The actions of the present compounds on cartilage of the joint are described in Examples in detail. It was recognized that the present compounds have the MMP-3 production inhibitory actions and the proteoglycan degradation inhibitory actions. Accordingly, it was suggested that the present compounds are useful as the therapeutic agents for the diseases in which MMP participates, particularly osteoarthritis.

Arthrogryposis occurs in the patients with osteoarthritis. Studying improvement effects of the present compounds on a mobility of a joint by using the rabbit-immobilized models, apparent improvement effects were recognized.

As described in the section of "Background Art", it is already known that the present compounds are useful as therapeutic agents for rheumatic diseases. However, osteoarthritis is a disease characterized by destruction of a joint accompanied by degeneration of cartilage in a joint due to aging and progressive degradation due to mechanical stress, and characterized by a proliferative change of bone cartilage, and differs from systemic autoimmune diseases such as the rheumatic diseases. Osteoarthritis differs from the rheumatic diseases also in that a synovial fluid is noninflammatory, abnormal remarks are scarcely observed in its peripheral blood, generally an erythrocyte sedimentation rate value and a CRP value are normal, and a rheumatic factor is negative.

Administration methods of drugs can be a method of administering the present compounds themselves as active compounds or a method of administering the present compounds in the form to be decomposed in vivo and to be converted into the active compounds, namely in the form of prodrugs. Both are widely used. The present compounds contain one carboxyl group and two thiol groups in their molecule. The present compounds themselves can be administered as active compounds, and the present compounds can be also administered with the above-mentioned groups protected with suitable protecting groups which can be converted into the active compounds in vivo, namely in the form of so-called prodrugs.

The present compound can be administered orally or parenterally. Examples of dosage forms are tablets, capsules, granules, powders, injections and the like. The present compound can be formulated into preparations by the conventional methods. For example, oral preparations such as tablets, capsules, granules and powders can be produced by adding optionally a diluent such as lactose, crystalline cellulose, starch or vegetable oil; a lubricant such as magnesium stearate or talc; a binder such as hydroxypropylcellulose or polyvinyl pyrrolidone; a disintegrator such as calcium carboxymethylcellulose or low-substituted hydroxypropylmethylcellulose; a coating agent such as hydroxypropylmethylcellulose, macrogol or silicone resin; or a film forming agent such as a gelatin film.

The dosage of the present compound can be selected suitably depending on symptoms, age, dosage form and the like. In case of the oral preparations, the present compound can be administered once to several times per day with a daily dose of 0.1 to 5000 mg, preferably 1 to 1000 mg.

Results of pharmacological tests are shown below. These do not limit the scope of the invention, but are intended to make the invention more clearly understandable.

BEST MODE FOR CARRYING OUT THE INVENTION

Pharmacological Tests

1. Actions on MMP-3 production of chondrocytes and degradation of proteoglycan

In order to study utility of the present compound, actions of the present compound on MMP-3 production and degradation of proteoglycan after IL-1β treatment were studied by using chondrocytes separated from femurs of rabbit knee joints according to the report of Nose et al. (J. Rheumatology, 24, 550–554 (1997)).

The action on MMP-3 production was studied by measuring MMP-3 activity. The action on degradation of proteoglycan was studied by measuring glycosaminoglycan (GAG) being a degradation product of proteoglycan.

Experimental Method

Preparation of Chondrocytes

Femurs of knee joints of male Japanese white rabbits were enucleated.

Surface cartilage of the femur was sliced into small pieces, and then tissues were dissociated by enzyme treatment to prepare chondrocytes.

Preparation of Medium A

A mammal cell culture basal medium D-MEM (Dulbecco's Modified Eagle Medium, produced by Gibco Co., Ltd.) containing β-ketoglutaric acid (5 μg/ml), L-ascorbic acid (50 μg/ml), lactoalbumin hydrolyzate (0.2 mg/ml), penicillin (100 U/ml) and streptomycin (100 μg/ml) (hereinafter referred to as "medium A") was prepared.

Preparation of Test Compound Solution

A test compound was dissolved in dimethyl sulfoxide (DMSO) ($1 \times 10^1$ M), and then a medium A containing IL-1β (1 ng/ml) (hereinafter referred to as "medium B") was added to this solution to dilute it so as to prepare a test compound solution having a prescribed concentration.

Using the medium B for a control group and the medium A for an untreated group, each experiment was carried out.

Test for Measuring Effect

Chondrocytes cultured in D-MEM to which fetal calf serum (10%), penicillin (100 U/ml) and streptomycin (100 μg/ml) had been added were seeded into 24-well culture plates ($1 \times 10^5$ cells/well) and cultured until reaching confluency.

IL-1β and the test compound were added by replacing the medium with the test compound solution (500 μl/well). The chondrocytes were cultured under conditions of 37° C. and 95% air 5% $CO_2$ for two days.

A culture supernatant was collected, and MMP-3 activity in the supernatant was measured with MMP-3 assay Kit (produced by Yagai Co., Ltd.).

A GAG concentration in the supernatant was measured according to the method of Farndale et al. (Biochim. Biophys. Acta, 883, 173–177 (1986)).

The action on MMP-3 production is represented by an MMP-3 production inhibition rate (%) at the prescribed concentration of the test compound.

Production inhibition rate (%)=[(A–B)/(A–C)]×100

A: MMP-3 activity of control group

B: MMP-3 activity of test compound solution-treated group

C: MMP-3 activity of untreated group

The action on degradation of proteoglycan is represented by a proteoglycan degradation inhibition rate (%) at the prescribed concentration of the test compound.

Degradation inhibition rate (%)=[(D–E)/(D –F)]×100

D: GAG concentration of control group

E: GAG concentration of test compound solution-treated group

F: GAG concentration of untreated group

Results

Table 1 shows the MMP-3 production inhibition rate (%) at the prescribed concentration of the test compound as one example of test results.

TABLE 1

| Test compound (concentration) | Production inhibition rate (%) |
|---|---|
| Bucillamine (3 μM) | 28 |

The value in the table is an average of three samples.

Table 2 shows the proteoglycan degradation inhibition rate (%) at the prescribed concentration of the test compound as one example of test results.

TABLE 2

| Test compound (concentration) | Degradation inhibition rate (%) |
|---|---|
| Bucillamine (3 μM) | 19 |

The value in the table is an average of three samples.

Tables 1 and 2 show that bucillamine exhibits inhibitory actions on MMP-3 production and proteoglycan degradation due to IL-1β stimulation.

2. Improvement effect on mobility of knee joint

In order to study in vivo effects of the present compound on osteoarthritis, an improvement effect on a mobility of a knee joint was investigated by using rabbit-immobilized models.

Experimental Method

Preparation of Test Compound Solution

A test compound was suspended in a 1% aqueous methyl cellulose solution to prepare test compound solutions having desired concentrations.

Test Method

Knee joints of right hind paws of NZW rabbits (13 weeks old, body weight: 2.97 to 3.27 kg) were fixed in an extended position with plaster bandages under sodium pentobarbital (25 mg/kg) anesthesia. Administering orally the test compound (amount of liquid to be administered: 10 ml/kg) to the rabbits for four weeks, the rabbits were sacrificed by exsanguination on the 29th day, and then mobilities of the knee joints were measured. A similar experiment was carried out by using a 1% aqueous methyl cellulose solution (10 ml/kg) as a control instead of the test compound.

Method of Measurement

The mobility of the knee joint was determined from a difference between a maximum flection angle obtained when a paw joint of the rabbit was vertically loaded with a load of 400 g and a maximum extension angle.

Results

Table 3 shows mobilities of the joint (degree) at the prescribed concentrations of the test compound as examples of test results. Bucillamine was used as the test compound of this test.

TABLE 3

| Test compound (mg/kg) | Mobility of knee joint (degree) |
|---|---|
| Control | 42 |
| 10 mg/kg | 46 |
| 30 mg/kg | 48 |
| 100 mg/kg | 53 |

Each value in the table is an average of ten samples.

Table 3 shows that bucillamine administration improves the mobility of the rabbit knee joint dose-dependently in the range of the dosage of this test.

The above-mentioned results of the pharmacological tests show that the present compound has the MMP-3 production inhibitory action, the proteoglycan degradation inhibitory action and the improvement effect on arthrogryposis. Accordingly, it is expected that the present compound is useful as a therapeutic agent for diseases in which MMP participates, particularly osteoarthritis.

Industrial Applicability

The present invention provides therapeutic agents for diseases in which MMP participates, particularly osteoarthritis, comprising mercaptoacylcysteine derivatives as active ingredients.

What is claimed is:

1. A method for treating osteoarthritis comprising administering to a patient in need thereof a pharmaceutically effective amount of a compound represented by the following formula [I] or a pharmaceutically acceptable salt thereof, alone or optionally with a pharmaceutically acceptable additive,

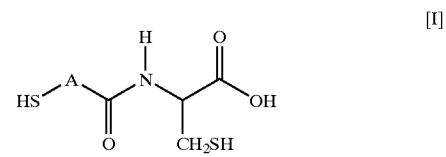

[I]

wherein "A" is a lower alkylene.

2. A method as claimed in claim 1, wherein "A" is —C(CH$_3$)$_2$.

3. The method as claimed in claim 1, wherein "A" is a straight-chain or branched alkylene having 1 to 6 carbon atoms.

* * * * *